United States Patent [19]

Moran

[11] Patent Number: 5,127,726
[45] Date of Patent: Jul. 7, 1992

[54] METHOD AND APPARATUS FOR LOW ANGLE, HIGH RESOLUTION SURFACE INSPECTION

[75] Inventor: Kevin E. Moran, Belmont, N.C.

[73] Assignee: Eastman Kodak Company, Rochester, N.Y.

[21] Appl. No.: 354,486

[22] Filed: May 19, 1989

[51] Int. Cl.⁵ .......................................... G01N 21/88
[52] U.S. Cl. ................................... 356/237; 250/563; 250/572
[58] Field of Search ................. 356/237; 250/563, 572

[56] References Cited

U.S. PATENT DOCUMENTS

| | | |
|---|---|---|
| 3,125,265 | 3/1964 | Warren et al. |
| 3,992,111 | 11/1976 | Roulier et al. |
| 4,030,827 | 6/1977 | Delhaye et al. |
| 4,184,082 | 1/1980 | Peoples |
| 4,342,515 | 8/1982 | Akiba et al. |
| 4,376,583 | 3/1983 | Alford et al. |
| 4,389,669 | 6/1983 | Epstein et al. |
| 4,417,149 | 11/1983 | Takeuchi et al. ................... 250/563 |
| 4,614,427 | 9/1986 | Koizumi et al. |
| 4,630,276 | 12/1986 | Moran |
| 4,669,875 | 6/1987 | Shiba et al. |

FOREIGN PATENT DOCUMENTS 0-398-781 11/1990 European Pat. Off.
62-11148 1/1987 Japan.

OTHER PUBLICATIONS

Surfscan ® Patterned Wafer Contamination Analyzer, Tencor Instruments, Printed Aug. 1988.
Hitachi Electronics Engineering Co., Ltd. brochure entitled "Patterned Wafer Inspection System HILI-S-200".

Primary Examiner—Richard A. Rosenberger
Attorney, Agent, or Firm—Bell, Seltzer, Park & Gibson

[57] ABSTRACT

The invention relates to an inspection system for inspecting the surfaces of wafers, LCD's and film substrates for flaws. The system includes a scanning laser inspection system for quickly inspecting the surface and identifying and locating the flaws. The system generates and displays a flaw map graphically illustrating the article surface and the respective locations of the flaws for subsequent optical inspection. The operator selects a flaw and an optical inspection system is positioned over the selected flaw to provide a magnified image of the flaw. The operator may optically inspect all or any number of the flaws. The invention also includes means for spectrometrically analyzing the reflected light to further identify the flaw.

16 Claims, 2 Drawing Sheets

METHOD AND APPARATUS FOR LOW ANGLE, HIGH RESOLUTION SURFACE INSPECTION

FIELD OF THE INVENTION

This invention relates to systems for inspecting the surface of an article and more particularly to systems for inspecting the surface of an article for microscopic flaws and debris.

BACKGROUND OF THE INVENTION

In the process of manufacturing a silicon microchip, light is directed through a reticle mask to etch circuits into a silicon wafer disc. The presence of dirt, dust, smudges, scratches or other flaws on the surface of the silicon wafer is highly undesirable and will adversely affect the resulting circuits. As a result, the silicon wafers are necessarily inspected prior to and during the manufacturing process. One common inspection technique is for a human inspector to visually examine the surface under intense light and magnification. However, the microscope has a small field of view so it takes a human inspector an extended period of time to visually examine the entire surface of the wafer.

Laser surface inspection devices have been developed for inspecting the surface of polished silicon wafers to accurately detect small particles or flaws. Examples of such devices are disclosed in Alford et al. U.S. Pat. No. 4,376,583 issued Mar. 15, 1983 and Moran U.S. Pat. No. 4,630,276 issued Dec. 16, 1986. In these known laser surface inspection systems, a laser beam is traversed across the surface of the silicon wafer and the reflections from the wafer are collected and analyzed to provide information about any flaws present on the wafer surface. The light is specularly reflected from the polished surface of the wafer, but in locations where the beam strikes surface flaws, the light is scattered. By separately collecting the scattered and specularly reflected light, the inspection device can quickly determine the size and locations of flaws on the surface of the wafer. This provides a satisfactory pass/fail test for inspecting the wafers, however, the nature and source of the flaws are not suitably analyzed by such laser inspection techniques. Also, when the wafer has been etched with a pattern to form the microchips the etching may provide spurious indications of flaws on the surface.

To inspect the patterned surface of silicon wafers, low angle laser surface inspection devices are employed, such as those disclosed in Koizumi et al. U.S. Pat. No. 4,614,427 and Shiba et al. U.S. Pat. No. 4,669,875 for example. These devices inspect the surfaces of patterned wafers using a laser beam at a low glancing angle. However, laser scanning does not provide sufficient resolution or clarity of the flaws to analyze the nature or source of the flaws in the surface.

Optical scanning arrangements are known which use optical lenses to microscopically view the surface and identify and analyze flaws in the surface. However, such systems produce enormous amounts of data and require powerful computers to process and analyze the data produced. Accordingly such systems are very expensive. Because of the small field of view and the enormous volume of data obtained, this type of system is relatively slow.

In one recently developed device, Hitachi model HILIS-200, foreign particles are detected by a low angle fixed spot laser beam. As the wafer rotates and translates under the laser beam, the particles are detected by an overhead photomultiplier and a map of the particles is formed. Subsequently, the foreign particles may be microscopically observed and photographed by repositioning the flaw under a microscopic viewing device. However, this requires a very accurate and reliable X-Y table to reposition the flaws in the field of view. Also, the process of inspecting the wafers by moving the wafer around under the fixed spot laser is slow and time consuming.

Accordingly, it is an object of the present invention to provide a system for inspecting a surface which efficiently identifies and analyzes flaws and which avoids the limitations and disadvantages of the prior art as noted above.

It is a further object of the present invention to provide a system which quickly identifies flaws on the surface of an article and interactively analyzes the identified flaws.

SUMMARY OF THE INVENTION

The above and other objects of the present invention are achieved by a method and apparatus which utilize a combination of laser scanning surface inspection and an optical microscopic inspection for quickly and efficiently analyzing and locating flaws over a relatively large portion of the surface of the article while enabling the operator to readily examine more closely selected flaws under high magnification. More particularly, the present invention provides an apparatus for inspecting the surface of an article comprising a transport for transporting the article past an inspection zone. A laser inspection means is positioned adjacent the inspection zone for scanning a laser light beam across a relatively large area of the article surface to detect flaws. A display means cooperating with the laser inspecting means displays to an operator of the apparatus a flaw map showing the locations of the detected flaws on the article surface. An optical inspection means is positioned adjacent the inspection zone for inspecting the article surface. The operator uses a selection means cooperating with the display means to allow the operator to select from the displayed flaw map a particular location on the article surface for closer inspection. The apparatus further has means responsive to the selection means and cooperating with the transport means for positioning the selected particular location on the article surface within the field of view of the optical inspection means so that the selected location can be optically inspected.

The apparatus may further include a spectrometer for providing analysis of the color characteristic of the flaws. Other features include magnification of the optical image of the flaws for visually analyzing the flaws.

BRIEF DESCRIPTION OF THE DRAWINGS

While some of the features and advantages of the invention have been stated, additional features and advantages will become apparent as the description of the invention proceeds when taken in conjunction with the following drawings in which—

DETAILED DESCRIPTION OF THE PREFERRED EMBODIMENT

Figure 1:
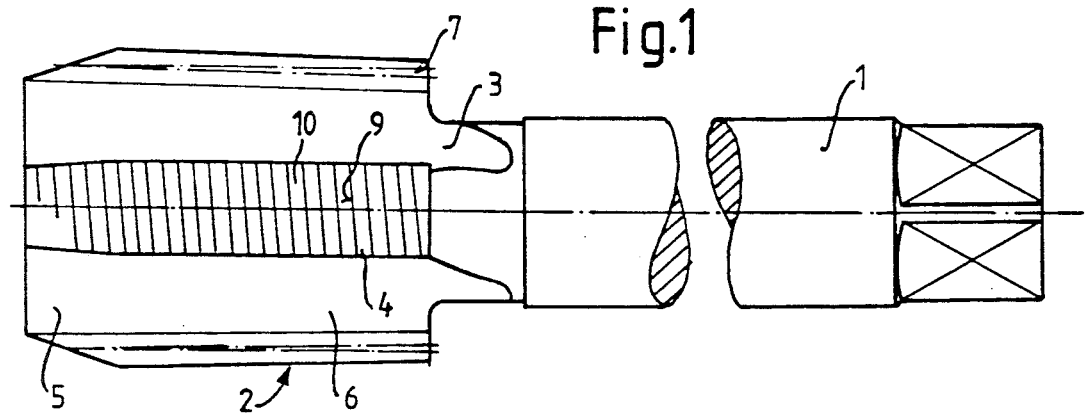
FIG. 1 is a front perspective view of a system embodying the features of the present invention.
Figure 2:
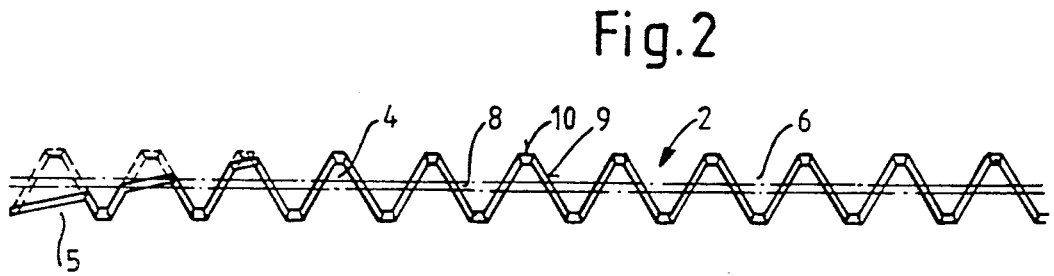
FIG. 2 is a schematic illustration of the system.

Referring now to the drawings, FIGS. 1 and 2 illustrate a surface inspection system, generally referred by the numeral 10, embodying the features of the present invention. The surface inspection system 10 is arranged to inspect the surfaces of silicon wafers to detect dirt, dust, smudges, scratches or other flaws. However, it should be recognized that the invention has broader applicability, and may be utilized for inspecting the surfaces of many types of articles such as liquid crystal displays (LCD's) and web substrates such as photographic film. Moreover, the invention may be embodied in many different forms. Accordingly, it should be understood that the specific embodiments described herein are illustrative of how the present invention may be practiced, and that the invention is not limited to these specific examples.

The system 10 is arranged as a workstation including a worktable 11. Positioned on the worktable 11 is a generally closed and substantially light proof housing 12, a pair of video displays 13 and 14, a keyboard 15, and a mouse 16. A cabinet 21 is suspended below the worktable 11 for carrying a system controller 40. Adjacent the cabinet 21 is a shelf unit 22 for carrying a printer 23 and associated printer paper.

The housing 12 has been partially broken away in FIG. 1 to better illustrate the inspection arrangement of the present invention. The inspection of the wafer W is conducted in an inspection zone 30 on an inspection table 31. The table is an X-Y table which is mounted for precise movement along both the X and Y horizontal axes. In an alternative embodiment the table 31 is an X-Y-Z-θ table which is able to move precisely in the X, Y and Z directions as well as being precisely rotated about the vertical Z axis. A robotic wafer handling device 32 is located adjacent the inspection station 30 to load and unload wafers from a cassette 33 onto the table 31. The cassette 33 holds a number of wafers and is loaded into the cabinet 12 through a door (not shown). The handling of the wafers inside the housing 12 is done automatically without contact by human hands to avoid contamination or smudges.

The inspection of the wafer W is accomplished by a laser inspection system generally indicated by the numeral 50 and by an optical inspection system generally indicated by the numeral 60. Referring to FIG. 2, the laser inspection system comprises a laser source 51 such as a low power helium-neon laser. The laser 51 is arranged to direct a laser beam through focusing lenses as known in the art to a scanning mirror 52 which deflects the laser beam along a predetermined oscillating scan pattern. The scanning mirror 52 may be of any suitable type known in the art, such as a rotating polygonal mirror or, as illustrated, an electrically reciprocated mirror (galvanomirror) driven by a galvo drive 52a.

The scanning laser beam is then directed to a folded optical cell comprised of mirrors 53a and 53b. The mirrors 53a and 53b are so configured and arranged as to effectively form a collimated scan pattern, such that the beam at one part of the scan is essentially parallel to the beam at other parts of the scan. Such a scan pattern may also be referred to as a telecentric scan. An example of a suitable folded optic cell is disclosed in greater detail in commonly owned Moran U.S. Pat. No. 4,630,276 which is incorporated by reference herein.

As illustrated in FIG. 2, the folded optical cell is so arranged that it directs the scanning laser beam to the inspection zone 30 at a low angle with respect to the wafer surface. In the preferred embodiment the angle of incidence is approximately 10°. Because the scanning laser beam moves in a substantially parallel or telecentric scan pattern as it traverses the wafer surface, the focal length of the beam does not vary significantly and the beam remains in sharp focus throughout the scan. Because the laser traverses the wafer surface very quickly, it appears to form a line across the surface of the wafer.

As the laser beam is scanned across the surface of the wafer W, the inspection table 31 moves the wafer W at a constant speed perpendicular to the scan line formed by the scanning laser beam. The scans of the laser beam thus sweep back and forth across the wafer surface as the wafer moves through the beam, and the entire surface of the wafer is scanned by the laser relatively quickly. For example, by this arrangement the surface of an 8" wafer may be scanned in approximately ten seconds.

As the surface of the wafer is scanned in the inspection zone 30, laser light is reflected by the wafer surface away from the laser light source at an angle generally corresponding to the low angle of incidence. However, if the surface has any flaws such as scratches or dirt on the surface, the flaws will reflect the laser light in a scattered randomly oriented pattern.

To detect the flaws, a light collector 57 is arranged to receive reflected light directed generally back toward the source of the laser light. The collector 57 includes a lens 55 to focus light in through fiber optic collectors to a photomultiplier tube. The photomultiplier tube converts the collected light signals into electrical signals for subsequent processing and analysis. An analog to digital unit (ADU) 57a converts the analog signals of the photomultiplier tube to digital signals for use by the system controller 40.

The laser inspection system 50 may also include in a preferred arrangement a polarizing lens 54 arranged in the path of the incident laser beam and a polarizing filter 56 arranged in the path of the reflected laser light reaching the collector 57. The orientation of the polarizing devices 54 and 56 can be adjusted to assist in filtering out background noise and false flaw signals, such as reflections from the pattern on the surface of the wafer W.

The optical inspection system 60 is arranged directly over the inspection station 30 with its viewing axis substantially perpendicular to the wafer surface to provide a magnified view of the flaws on the wafer W. The optical inspection system 60 includes a video camera 61 provided with one or more focusing and magnifying lenses 62 with filters 63. The optical inspection system 60 may be operated using the light from the laser 51. However, a white light source 64 is also provided to give auxiliary illumination for the video camera 61. The image received by the camera 61 is displayed by video display monitor 14. However, as indicated in broken lines in FIG. 2, the system 10 may optionally include a direct view eyepiece 65.

The system 10 is computer controlled by a system controller 40. The system controller 40 operates the inspection system 10 under the supervision and direction of a human operator, stores and retrieves data generated by the inspection systems 50 and 60 and performs data analysis. As illustrated in FIG. 2, the system controller 40 includes many components. In the arrangement illustrated, the system controller 40 is an IBM PC AT-compatible computer with specialized circuit boards to handle the various control and analysis functions of the system 10. The system controller 40 includes a main central processing unit 41 with input and output devices including a keyboard 15, a mouse 16, a removable diskette drive 41a, a hard disk 41b, and a printer 23. The keyboard 15 is preferably an enhanced AT-style keyboard. The mouse 16 includes three separate buttons so that a substantial portion of the operator's tasks may be performed strictly by using the mouse in connection with the user interface displayed on the graphics monitor 13 as will be discussed below. The printer 23 is preferably a high resolution, color ink jet printer to print hard copy images of the flaw maps and magnified images of individual flaws as will be explained in more detail below.

Figure 3:
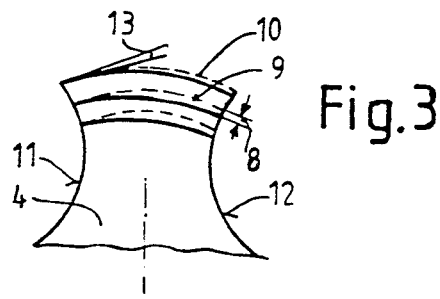
FIG. 3 is an example illustration of a computer display produced by the system.
Figure 4:
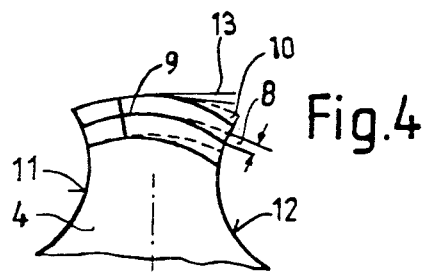
Figure 5:
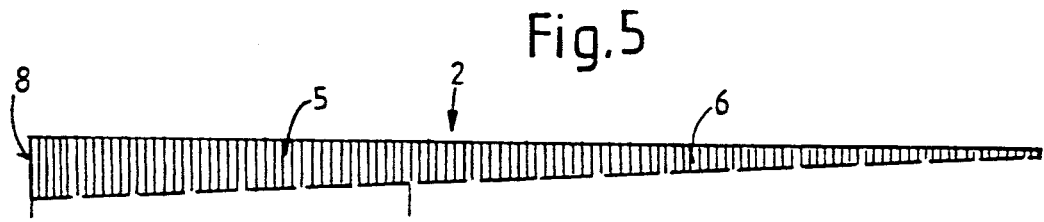
Figure 6:
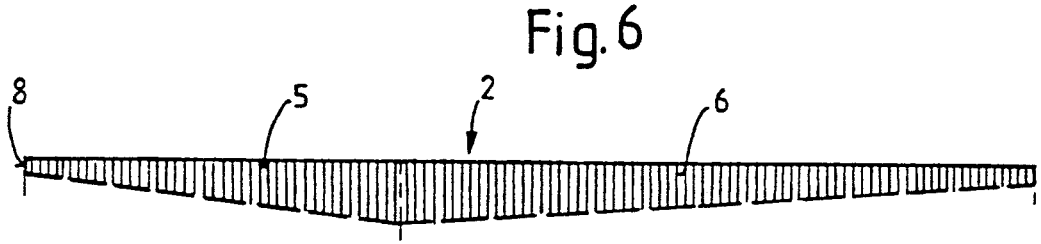
Figure 2:
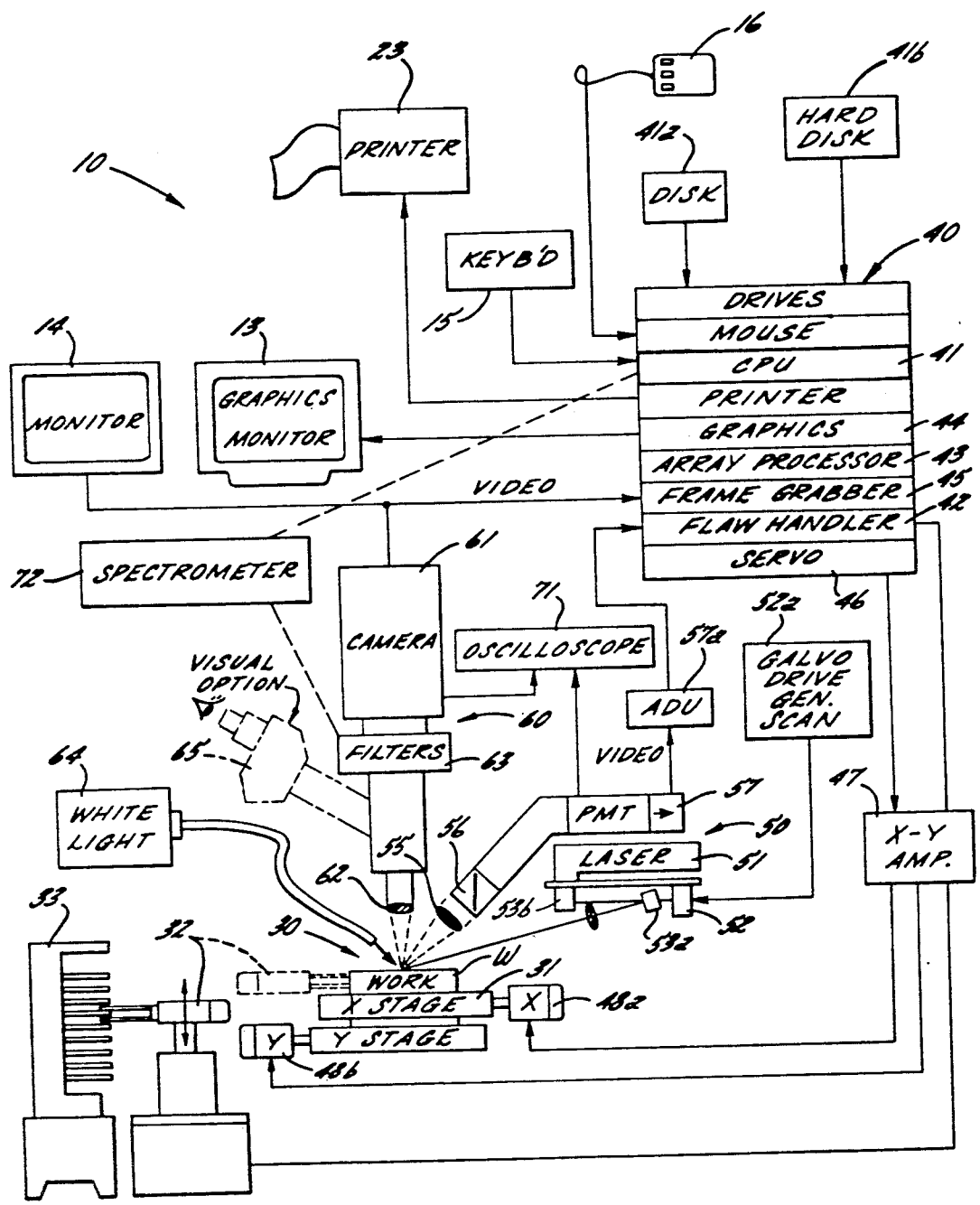
Figure 1:
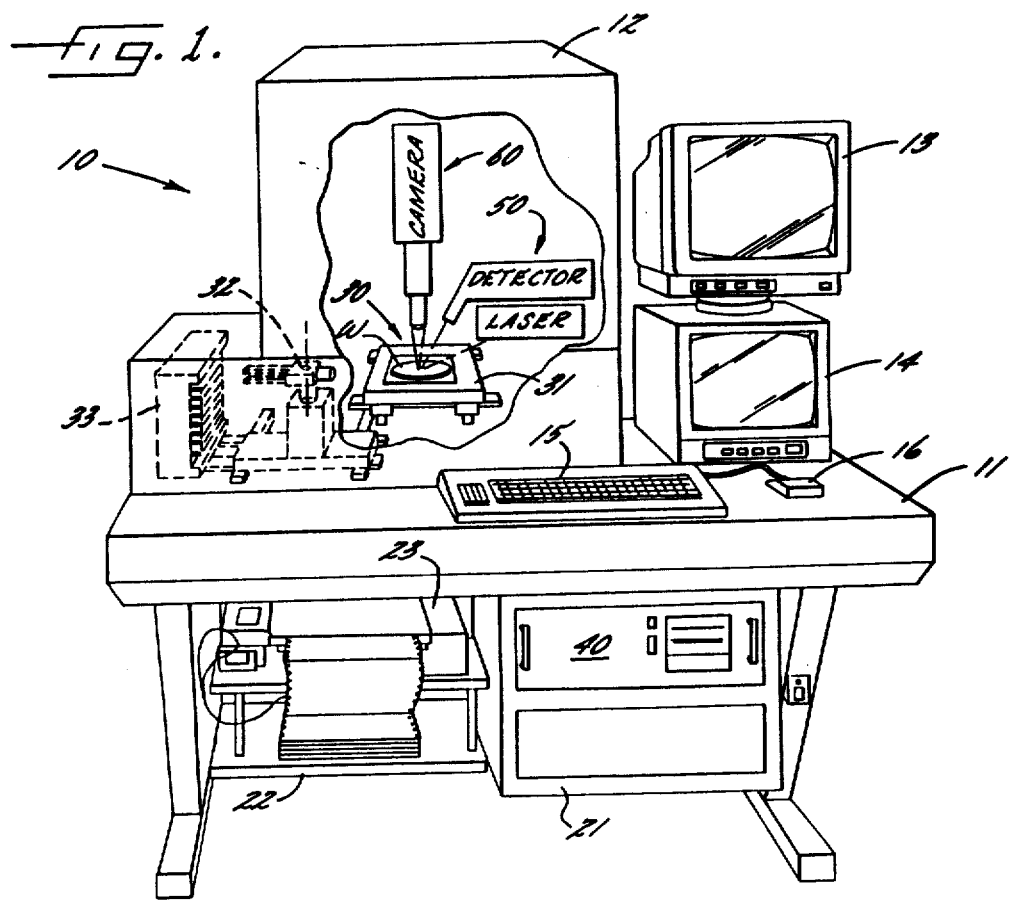
Figure 3:
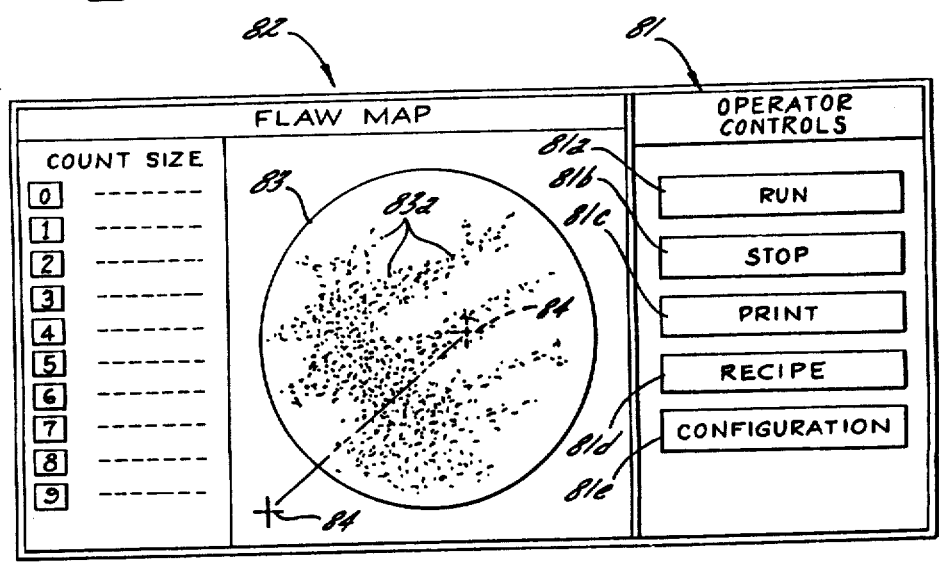

The system controller 40 further includes a servo control board 46 which provides an output signal to a servo amplifier 47 for controlling operation of X and Y axis motors 48a, 48b associated with the inspection table 31 and for also controlling operation of the wafer handling device 31. In addition, the system controller 40 includes a flaw handler printed circuit board 42 which receives flaw data from the analog to digital unit 57a and assembles the data into scan lines for use by the array processor 43. The assembled flaw data is transferred to the array processor 43 which functions to count the flaws, sort them into user-defined bins, perform edge exclusion, eliminate double-pixeling and assess scratches and haze on the article surface. The array processor 43 preferably comprises a Motorola 68020 based CPU with an associated math coprocessor and substantial random access memory. The processed flaw data is then sent back to the CPU 41. A high resolution graphics controller 44 assimilates flaw data from the CPU 41 and graphically displays, by means of a high resolution graphics monitor 13, a flaw map and other operational information regarding the system 10 as illustrated in FIG. 3. A frame grabber 45 receives the video image of the wafer from the video camera 61 and digitizes the image to be maintained in storage, to be displayed on video monitor 14 or printed onto hard copy paper by a printer 23.

The system controller 40 also includes system software operable by the user for configuring the system, controlling the motion of the wafer handling device 32, the laser and optical inspection systems 50, 60, and presenting the collected data via various user-selectable display screens. Movement between screens and machine control is performed with the use of pop-up menus which can be operated by the mouse 16 and/or by keyboard commands. Data such as flaw counts, wafer matrix, statistics, and wafer classification (i.e. ACCEPT or REJECT) are presented on the graphics monitor 13 or as hard copy output from the printer 23. The system controller 40 is further adapted to store data by suitable means such as a removable diskette drive 41a or a hard disk 41b for subsequent recall and analysis. Such data may include, in addition to the data discussed above, the flaw map data obtained from the laser inspection system 50, and digitized images of the flaws obtained from the optical inspection system 60, as well as the coordinate locations for the flaws.

The system further includes an oscilloscope 71 used for identifying and verifying flaws so that flaws selected for optical inspection are accurately positioned in the field of view of the optical inspection means 60. The oscilloscope 71 has input channels from each of the video camera 61 and the fiber optic collector 57. The oscilloscope 71 may then compare the signals received by the camera 61 with the signals received from collector 57. The output of the oscilloscope 71 is provided on its own display and used by the operator to direct the X-Y table to the correct position of the selected flaw.

The system 10 also has a third level of inspection, after the laser inspection and the optical inspection. The system 10 includes a spectrometer 72 to analyze detected flaws based upon the colors of light reflected. Different materials and substances have different and sometimes characteristic color reflections. Identifying the characteristic color of the debris on the wafer W may enable the operator to determine whether the debris is harmless or harmful. Also knowing the material may quickly isolate the source of contamination. This data may also be stored by the system controller 40 with the data of the coordinates and digitized images of each flaw for subsequent recall, review and analysis. It should be quite apparent that the potential cost savings for manufacturers of wafers is quite substantial if sources of contamination are readily identified and abated.

Referring now to FIG. 3, there is shown an example illustration of a computer display produced by the system 10. The display is provided by the graphics monitor 13 which is preferably a color video display monitor. The system 10 includes a highly adaptable graphics display including windowing options to provide maximum adjustability for an operator. In FIG. 3 is illustrated an operator control display 81 and a flaw map 82. The system 10 may also display flaw information in a histogram or other graphic form. The flaw map 82 is, as discussed above, generated from flaw data generated by the laser scanning system 50. The map includes a general representation of the surface of the wafer 83 with the flaws indicated each by dots 83a. Alternatively the dots 83a may be indicated by various colors or shapes (such as stars, squares, triangles, etc.) depending on the size or other feature of the flaw. The operator selects a particular flaw on the flaw map by pointing to the flaw with cursor 84. The cursor is moved by moving the mouse 16 around on the table 11. Once a particular location is selected, one of the buttons on the mouse is pressed to indicate to the system 10 the particular selection. For example, the cursor is illustrated in broken lines pointing out a particular location on the wafer for closer inspection. The cursor may also be used to push the buttons in the operator control display 81 by pointing with the cursor similar to selecting a flaw. For example, when the operator wants to print out a hard copy of the flaw map, the cursor 84 is moved to the print button on the screen and one of the buttons on the mouse is pressed. The system 10 would then provide a hard copy print out from the printer 23 of the flaw map.

The operation of the system 10 begins with placing a cassette 33 of wafers in the housing 12. The operator instructs the system to inspect according to a particular recipe (operating parameters). The recipe may be previously stored on a disk and generally includes such data as the size and thickness of the object being inspected, flaw categories to be detected, and other variables regarding the inspection process. In most cases the recipes will be standardized and stored on the hard disk 41b under identifying recipe names. The various recipes would be accessible by the operator by pressing the recipe button 81d on the operator control display 81.

The inspection process begins by the operator pressing the run button 81a on the operator control display 81. The system controller 40 then directs the wafer handler 32 to load the first wafer from the cassette 33 onto the inspection table 31. The laser inspection system 50 is activated and the inspection table 31 transports the wafer W along the inspection Zone 30 until the entire surface has been scanned. The flaw data generated from the laser inspection is sorted, analyzed, and stored by the system controller 40 to generate a flaw map. The flaw map is displayed on the graphics monitor 13 in a form similar to that shown in FIG. 3 indicating the flaws and their respective locations.

The operator, using the mouse 16, may then select a particular flaw from the flaw map for closer inspection by moving the mouse 16 so as to position the cross hair cursor 84 onto the selected flaw and then clicking one of the mouse buttons. In response to this selection, the system controller 40 actuates the X-Y axis motors 48a 48b associated with the inspection table 31 to move the table as necessary along the X and Y axes in order to locate the coordinates of the selected flaw within the field of view of the lens 62 of the optical inspection system 60. As the coordinates of the selected flaw approach the field of view of the optical inspection system 60, the laser inspection system 50 scans the wafer surface to verify that the selected flaw is accurately positioned in the field of view. An oscilloscope 71 also may be used by the operator to verify that the selected flaw is centered in the field of view. Alternatively the system controller 40 may separately verify the flaw location. The stored data for the selected flaw includes the precise data for the scan which detected the flaw. By comparing the stored data of the scan with the current scan being directed across the wafer the selected flaw would then be identified by the current scan. At the same time, the system controller 40 monitors the light signals received by each of the video camera 61 and the collector 57. The system controller 40 can very quickly bring the selected flaw into the field of view of the camera by comparing the timing of the two signals with the oscilloscope 71. In other words, if the reflected light entering the camera 61 is coincident with the timing of the reflected light from the selected flaw, then the selected flaw is in the field of view of the camera. If the timing is not coincident, then the inspection table needs to adjust the position of the wafer. If the flaw is not along the scan line but lateral to it, the operator using the cursor would need to indicate to the system 10 to move the wafer slightly in directions lateral to the scan line. Once the laser inspection system detects the selected flaw, the system controller 40 quickly directs the inspection table 31 to provide the flaw in the field of view as before. As a practical matter the detecting and verifying step is very quick since the table 31 generally positions the selected flaw very close to the field of view.

Once the selected flaw is within the field of view the camera provides a magnified image of the flaw on the display monitor 14. The operator visually assesses the flaw and indicates its status to the system 10. The visual inspection often reveals the type of material of the flaw.

One particularly advantageous feature of the present invention is that during the optical inspection of the wafer, the laser continues to scan the object at the low angle. At the same time, white light from the white light source 64 is directed virtually straight down onto the surface. Since the laser beam is a distinctive red, the feature on the surface which has been detected as a flaw is illuminated in the red laser light distinguishing it from the remaining area of the field of view which is illuminated strictly in white light. (Remember that the low angle laser is only reflected to the camera 61 and the collector 57 by a flaw.)

After the optical analysis of each flaw, the flaw may then be spectrometrically analyzed by the spectrometer 72. The spectrometer 72, in cooperation with the optical inspection system 60, analyzes the color spectrum of white light reflected by the selected flaw. The results of the spectrometric breakdown of the light are provided to the system controller 40 for further analysis, comparison and storage. This provides information characterizing the flaw in addition to the optical inspection.

The operator steps through a series of selected flaws using the two video displays 13 and 14. Once the inspection of a wafer is complete the operator may stop the inspection by button 81b. The robotic wafer handler 32 then removes the wafer from the table 31 and returns it to the cassette 33. A second wafer W is then removed by the robotic wafer handler 32 and is placed on the table 31 for inspection.

In some applications, the overall size of the inspection surface may be larger than the maximum field of view of the laser inspection system 50. In such circumstances the surface may be subdivided into separate areas or zones, with the inspection table being successively indexed to position the respective areas or zones within the field of view. The operator may configure the inspection by button 81e and defining the areas by defining windows with the cursor.

The efficiency of the inspection method of the present invention of primary importance to the invention. The laser inspection means searches an area of approximately 200 mm×200 mm in about ten seconds. The optical inspection is thereafter inspecting areas on the wafer of approximately one square millimeter. This is a very small area of the article surface, however, it is inspecting areas where there is an indication of a flaw. Therefore at the end of the inspection process, the entire wafer has been inspected; there are no potential areas that were missed; the flaws that were detected have been carefully considered under high magnification, and it was accomplished relatively quickly (i.e. approximately 1-3 minutes total).

That which is claimed is:

1. An apparatus for inspecting the surface of an article for flaws, comprising:

transport means for transporting the article along a predetermined path of travel past an inspection zone;

laser inspection means positioned adjacent the inspection zone for detecting flaws on the article surface, and including means for directing a laser beam in a predetermined scan path at a relatively low angle to the article surface during movement of the article by said transport means past the inspection zone, and detector means positioned for receiving laser energy reflected from the surface of the article;

means cooperating with said detector means for analyzing the reflected laser energy and for generating data identifying flaws and their corresponding locations on the article surface;

flaw map display means for receiving the thus produced data and for displaying to the operator of the apparatus a flaw map showing the locations of the detected flaws on the article surface;

optical inspection means positioned adjacent the inspection zone for inspecting the article surface, and including a video camera, an optical microscope lens connected to said camera, and a video display operatively connected to said video camera for displaying a high magnification view of the article surface;

operator actuable selection means cooperating with said flaw map display means to allow the operator to indicate directly on the displayed flaw map a particular flaw on the article surface for closer inspection;

positioning means responsive to said selection means and cooperating with said transport means for positioning the article such that the selected flaw is within the field of view of said optical inspection means so that the selected flaw can be optically inspected at high magnification; and spectrometer means cooperating with said optical inspection means to permit analyzing the color characteristics of the selected flaw.

2. An apparatus as defined in claim 1 additionally including means for storing data from the spectrometer analysis of the selected flaw.

3. An apparatus for inspecting a patterned surface of an article for flaws, comprising:

transport means for transporting the article along a predetermined path of travel past an inspection zone;

laser inspection means positioned adjacent the inspection zone for detecting flaws on the article surface, and including means for directing a polarized laser beam in a predetermined scan path at a relatively low angle to the article surface during movement of the article by said transport means past the inspection zone, and detector means including polarizing filter means positioned for receiving laser energy reflected from the surface of the article;

means cooperating with said detector means for analyzing the reflected laser energy and for generating data identifying the flaws and their corresponding locations on the article surface;

flaw map display means for receiving the thus produced data and for displaying to the operator of the apparatus a flaw map showing the locations of the detected flaws on the article surface;

optical inspection means positioned adjacent the inspection zone for inspecting the article surface, and including a video camera, an optical microscope lens connected to said camera, and a video display operatively connected to said video camera for displaying a high magnification view of the article surface and wherein said optical inspection means is mounted with a viewing axis oriented substantially normal to the article surface;

operator actuable selection means cooperating with said flaw map display means to allow the operator to indicate directly on the displayed flaw map a particular flaw on the article surface for closer inspection;

positioning means responsive to said selection means and cooperating with said transport means for positioning the article such that the selected flaw is within the field of view of said optical inspection means so that the selected flaw can be optically inspected at high magnification; and spectrometer means cooperating with said optical inspection means to permit analyzing the color characteristics of the selected flaw.

4. An apparatus as defined in claim 3 wherein said detector means is positioned at an acute angle with respect to said laser beam directing means so as to receive light reflected generally back toward said laser beam directing means.

5. A method for inspecting the surface of an article for flaws, comprising the steps of:

directing a laser light beam over the surface of the article in a predetermined scan path and generating data therefrom identifying flaws on the article surface;

displaying the thus obtained data in the form of a flaw map showing the locations of the flaws on the article surface;

receiving operator input directly on the displayed flaw map of a selected particular location on the article surface for closer inspection and in response thereto positioning the selected particular location on the article surface within the field of view of an optical inspection means; and optically inspecting the article surface, said step of optically inspecting the article surface including focusing white light on the article surface and spectrometrically analyzing the light reflected by the flaw.

6. A method as defined in claim 5 wherein said step of directing a laser light beam over the surface of the article comprises transporting the article along a predetermined path of travel past an inspection zone while scanning the laser light beam successively along a predetermined scan line and while detecting laser light reflected from the article surface.

7. A method as defined in claim 5 wherein said step of optically inspecting the article surface includes directing white light on the article surface and magnifying the optical image of the particular location.

8. A method as defined in claim 5 wherein said step of optically inspecting the article surface includes directing a video camera on the article surface and displaying the optical image on a video display.

9. A method as defined in claim 8 wherein said step of displaying the optical image on a video display comprises displaying a high magnification view of a relatively small area of the article surface while also displaying a larger area of the article surface on said flaw map.

10. A method as defined in claim 5 wherein said step of directing a laser light beam includes directing the laser beam in a predetermined scan path at a relatively low angle to the article surface.

11. A method defined in claim 5 further including the step of storing the data identifying the flaws and their corresponding locations for subsequent use in positioning a selected flaw within the field of view of the optical inspection means.

12. A method according to claim 11 wherein the step of positioning the selected flaw comprises again scanning the article surface with the laser light beam as the article is moved to verify that the selected flaw is positioned within the field of view.

13. A method as defined in claim 5 wherein the step of displaying a map comprises displaying the map on a video display screen and wherein the step of receiving operator input of a selected particular location further comprises receiving operator input of a particular flaw in cooperation with the video display screen and positioning the particular location of the selected flaw within the field of view of the optical inspection means.

14. A method as defined in claim 5 further including the step of storing data from the spectrometric analysis of the flaw.

15. An apparatus for inspecting the surface of an article for flaws, comprising:

transport means for transporting the article along a predetermined path of travel past an inspection zone;

laser inspection means positioned adjacent the inspection zone for detecting flaws on the article surface, and including means for directing a laser beam in a predetermined scan path at a relatively low angle to the article surface during movement of the article by said transport means past the inspection zone, and detector means positioned for receiving laser energy reflected from the surface of the article;

means cooperating with said detector means for analyzing the reflected laser energy and for generating data identifying flaws and their corresponding locations on the article surface;

flaw map display means for receiving the thus produced data and for displaying to the operator of the apparatus a flaw map showing the locations of the detected flaws on the article surface;

optical inspection means positioned adjacent the inspection zone for inspecting the article surface, and including a video camera, an optical microscope lens connected to said camera, and a video display operatively connected to said video camera for displaying a high magnification view of the article surface;

operator actuable selection means cooperating with said flaw map display means to allow the operator to select from the displayed flaw map a particular flaw on the article surface for closer inspection;

positioning means responsive to said selection means and cooperating with said transport means for positioning the article such that the selected flaw is within the field of view of said optical inspection means so that the selected flaw can be optically inspected at high magnification; and spectrometer means cooperating with said optical inspection means to permit analyzing the color characteristics of the selected flaw.

16. A method for inspecting the surface of an article for flaws, comprising the steps of:

directing a laser light beam over the surface of the article in predetermined scan path generating data therefrom identifying flaws on the article surface;

displaying the thus obtained data on a video display screen in the form of a flaw map showing the locations of the flaws on the article surface;

receiving operator input of a selected particular location on the article surface for closer inspection and in response thereto positioning the particular location of the selected flaw within the field of view of the optical inspection means; and optically inspecting the article surface;

wherein the step of optically inspecting the article surface further comprises focusing white light on the article surface and spectrometrically analyzing the light reflected by the flaw.

* * * * *

UNITED STATES PATENT AND TRADEMARK OFFICE
CERTIFICATE OF CORRECTION

PATENT NO.  : 5,127,726

DATED       : July 7, 1992

INVENTOR(S) : Kevin E. Moran

It is certified that error appears in the above-indentified patent and that said Letters Patent is hereby corrected as shown below:

Sheet 1 of 2 of the drawings should be deleted to appear as shown on the attached page.

Signed and Sealed this

Twenty-eighth Day of September, 1993

Attest:

BRUCE LEHMAN

*Attesting Officer*  *Commissioner of Patents and Trademarks*